United States Patent
Husheer

(10) Patent No.: US 8,540,644 B2
(45) Date of Patent: Sep. 24, 2013

(54) SYSTEM AND METHOD FOR ESTIMATING A BASAL BODY TEMPERATURE AND FORMING AN INDICATION OF OVULATION

(75) Inventor: Shamus Husheer, Cambridge (GB)

(73) Assignee: Cambridge Temperature Concepts Limited, Cambridge (GB)

( * ) Notice: Subject to any disclaimer, the term of this patent is extended or adjusted under 35 U.S.C. 154(b) by 638 days.

(21) Appl. No.: 12/299,056

(22) PCT Filed: May 4, 2007

(86) PCT No.: PCT/IB2007/001822
§ 371 (c)(1),
(2), (4) Date: Oct. 30, 2008

(87) PCT Pub. No.: WO2008/035151
PCT Pub. Date: Mar. 27, 2008

(65) Prior Publication Data
US 2009/0234200 A1   Sep. 17, 2009

(30) Foreign Application Priority Data
May 4, 2006   (GB) .................................. 0608829.8

(51) Int. Cl.
*A61B 5/00*   (2006.01)
*A61B 10/00*   (2006.01)
*G01N 33/48*   (2006.01)
*G01N 33/50*   (2006.01)
*G01K 1/00*   (2006.01)
*G01K 3/00*   (2006.01)

(52) U.S. Cl.
USPC ............. 600/549; 600/551; 702/19; 374/100; 374/104

(58) Field of Classification Search
USPC ......... 600/549, 551, 412, 438, 474; 374/100, 374/102, 104, 107; 702/19
See application file for complete search history.

(56) References Cited

U.S. PATENT DOCUMENTS 4,465,077 A * 8/1984 Schneider ..................... 600/551
4,509,531 A   4/1985 Ward
(Continued)

FOREIGN PATENT DOCUMENTS

DE   103 45 282 B3   4/2005
DE   199 43 456 B4   10/2005
(Continued)

OTHER PUBLICATIONS

Babycomp and Ladycomp, HTTP://www.ladycomp.co.uk/introduction ladycomp.htm, Jan. 27, 2009.
(Continued)

*Primary Examiner* — Max Hindenburg
*Assistant Examiner* — John Pani
(74) *Attorney, Agent, or Firm* — Novak Druce Connolly Bove + Quigg LLP; Vincent M DeLuca

(57) ABSTRACT

A data logger device for in-situ measurement of one or more physical parameters comprising a power source; one or more sensors for measuring the one or more physical parameters; a data store for storing representations of at least some of the measured values of the one or more physical parameters; control logic arranged to write the representations of at least some of the measured values to the data store and arranged to read data from the data store during data transmission; an antenna; and a transmitter coupled to the antenna and configured to transmit the stored data by passive transmission. The physical parameter may be temperature. A processor may estimate basal body temperature by extrapolating from a plurality of temperature readings during a sleep period. The estimated basal temperature may be used to form an indication of ovulation.

27 Claims, 6 Drawing Sheets

(56) References Cited

U.S. PATENT DOCUMENTS

| | | | |
|---|---|---|---|
| 4,549,819 A | 10/1985 | Muramoto et al. | |
| 4,676,254 A | 6/1987 | Frohn | |
| 4,771,791 A * | 9/1988 | Kubouchi | 600/549 |
| 6,270,252 B1 * | 8/2001 | Siefert | 374/102 |
| 6,478,748 B1 | 11/2002 | Kuhn et al. | |
| 6,814,706 B2 | 11/2004 | Barton et al. | |
| 7,015,826 B1 | 3/2006 | Chan et al. | |
| 7,148,803 B2 | 12/2006 | Bandy et al. | |
| 2002/0016553 A1 | 2/2002 | Tamaki et al. | |
| 2003/0069714 A1 | 4/2003 | Wigley et al. | |
| 2003/0210146 A1 | 11/2003 | Tseng | |
| 2004/0102815 A1 * | 5/2004 | Balczewski et al. | 607/17 |
| 2004/0152957 A1 | 8/2004 | Stivoric et al. | |
| 2004/0171964 A1 | 9/2004 | Heitz | |
| 2004/0215098 A1 | 10/2004 | Barton et al. | |
| 2004/0242976 A1 | 12/2004 | Abreu | |
| 2005/0059870 A1 * | 3/2005 | Aceti | 600/340 |
| 2005/0096558 A1 | 5/2005 | Friedman et al. | |
| 2005/0245839 A1 * | 11/2005 | Stivoric et al. | 600/549 |
| 2006/0070650 A1 | 4/2006 | Fraden | |
| 2007/0191729 A1 * | 8/2007 | Park et al. | 600/551 |

FOREIGN PATENT DOCUMENTS

| | | |
|---|---|---|
| EP | 0 195 207 A1 | 9/1986 |
| EP | 0 619 123 A2 | 10/1994 |
| EP | 1 593 946 A1 | 11/2005 |
| GB | 2186977 A | 8/1987 |
| GB | 2 416 633 A | 2/2006 |
| JP | 2001-353157 A | 12/2001 |
| JP | 2001-353158 A | 12/2001 |
| JP | 2001-353159 A | 12/2001 |
| JP | 2001-353160 A | 12/2001 |
| JP | 2004-163391 A | 6/2004 |
| JP | 2005-164405 A | 6/2005 |
| WO | 01/84518 A1 | 11/2001 |
| WO | 2005/032338 A2 | 4/2005 |
| WO | 2005/092177 A1 | 10/2005 |

OTHER PUBLICATIONS

Ciarcia, "Build A Low-Power Data Logger," Circuit Cellar Ink, Building Automation Section, pp. s12-s22.

Olsen et al., "A data logger tag for the study of slaughter procedures in aquacultured salmon," Hydrobiologia, Advances in Invertebrates and Fish Telemetry, 1998, vol. 371-372, pp. 71-77, Kluwer Academic Publishers, Belgium.

Wim Claes et al., Design of Wireless Autonomous Data Logger ICs, 2005, Springer of The Netherlands.

Van Marken Lichtenbelt et al., Evaluation of Wireless Determination of Skin Temperature Using iButtons, Journal of Physiology and Behavior, 2006, pp. 489-497, vol. 88, Elsevier.

De La Fuente Ruz et al., RFID Smart Temperature Sensor, Application in monitoring and traceability of hemoderivates, Mar. 13, 2007, EU RFID Forum, Brussels, Belgium; http://www.rfidconvocation.eu/Papersnotpresented/RFIDSmartTemperatureSenso.pdf.

Machine Translation of DE 199 43 456.

Japanese Notification of Reason for Rejection dated Jul. 10, 2012, in corresponding Japanese application.

* cited by examiner

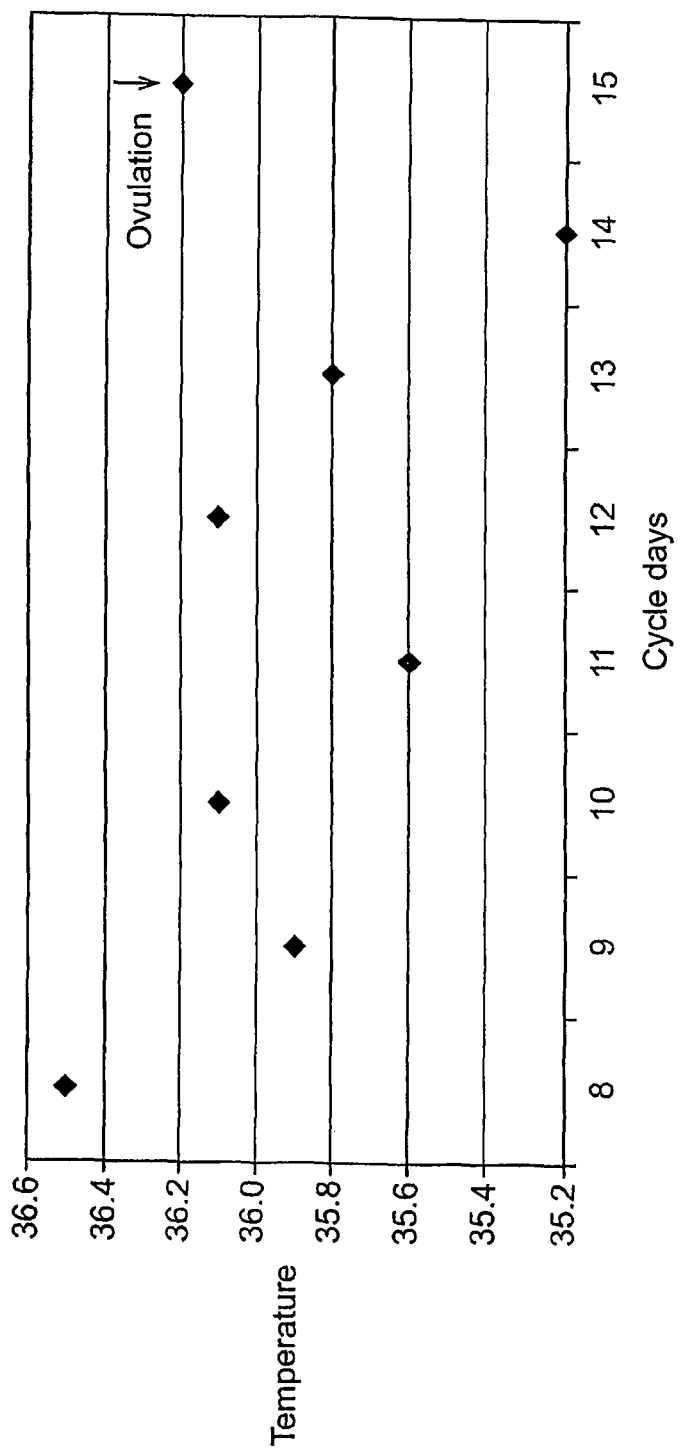
FIG. 6(contd.)

SYSTEM AND METHOD FOR ESTIMATING A BASAL BODY TEMPERATURE AND FORMING AN INDICATION OF OVULATION

This invention relates to a data logger device for in-situ measurement of one or more physical parameters, to a system for in-situ measurement of one or more physical parameters, to a system for determining the point of ovulation in a female, and to a system for in-situ measurement of temperature.

Data logger devices for measuring and storing physical parameters are widely used across the engineering and scientific worlds. Such devices allow the automated monitoring of physical parameters in-situ over long timescales, in difficult to reach locations or in environmentally dangerous conditions—situations in which manual measurements may be inconvenient or overly time-consuming.

One such data logging system that has been developed is the MiniMitter system for logging temperature. However the cost of the total solution is rather high, and the data logger itself is rather cumbersome and too large for many applications.

In particular, the periodic measurement of various physiological parameters is essential for many medical conditions, the parameters ranging from body fluid pressure and conductance to temperature and temperature gradients. Physiological parameters may be measured "by hand", for example by a doctor or nurse, or may be monitored by (often expensive) medical apparatus to which a patient is required to remain connected for the duration that the measurement in question is required.

The situation is even more acute for those people who are required to measure certain physiological parameters in a home environment (such as diabetics). Without the support structures in place at a clinic or hospital, patients are more likely to forget to take the required measurements, or they may find it inconvenient at times, and they may not be able to afford the medical equipment in the first place.

There is therefore a need for inexpensive, automated logging of physiological parameters by in-situ measurement devices. Such devices could reduce the burden on medical staff, reduce the possibility of measurements being missed and, because a device would remain in-situ at the required measurement location, would potentially reduce the number of painful or invasive measurements that a patient has to endure. Furthermore, measurements may be taken without interruption to the patient, for example, during sleep or a busy daily schedule.

For certain physiological parameters, or long-term medical conditions, an implantable device would best facilitate the measurement of these parameters. It is desirable for implanted medical devices to have as long a lifetime as possible within the patient, in as small as possible volume. In many devices, this is limited by a trade-off between battery life and battery size, and necessitates removal and reinsertion of the device simply for the purposes of recharging or replacing this battery. This causes undue stress and discomfort for the patient.

In particular, women will sometimes wish to regularly measure their body temperature in order to determine the point at which they are likely to ovulate each month. This "natural method" is attractive to many women who are seeking to conceive and can also be used as a way of avoiding pregnancy, perhaps by women with particular religious beliefs. For the most reliable results, regular temperature measurements are required over most of the ovulation cycle.

European Patent Application No. 0195207 describes a uterine implant for periodic logging of temperature data, which is wirelessly transmitted to a receiver on demand for analysis and display. This solves a significant problem in the use of the Basal Body Temperature (BBT) method for natural family planning, in that the user need not wake for, nor even remember to take temperature measurements, on a daily basis. Unfortunately the device must be periodically withdrawn and reinserted due to the need to replace or recharge the battery in the device. Although introduced into an accessible body cavity, this withdrawal and reinsertion procedure is highly inconvenient and has significant associated medical risks.

Alternatively, one could use an implant device that does not store the data measurements at the implant device but transmits the measurements directly to a reader. In this case the power for the implant may be supplied by the reader, such as in European Patent Application No. 0476730. This is common for passive radio-frequency identification (RF-ID) sensors. However, this set-up requires that the implant be located close to the RF-ID reader whenever the implant device is to make measurements.

In data logging systems that use a rechargeable battery the battery life is limited since a battery will only accommodate a certain number of recharge cycles before the battery performance declines to a level at which it cannot sustain a reasonable charge for operation of the data logger. This is a particular problem for an implanted data logger, for which a lifetime of the order of 10 years is desired to keep the required frequency of minor operations to replace the implant to a minimum.

A passive system has been suggested in European Patent Application No. 0746040, which describes a passive transponder that includes an integrated sensor. The transponder is operable to receive an interrogation signal from a scanner and to transmit identification information and body characteristic information to the scanner. However, the system does not provide data logging capabilities and therefore requires the scanner to be coupled to the transponder whenever measurements are required.

According to a first aspect of the present invention there is provided a data logger device for in-situ measurement of one or more physical parameters comprising: a power source; one or more sensors for measuring the one or more physical parameters; a data store for storing representations of at least some of the measured values of the one or more physical parameters; control logic arranged to write the representations of at least some of the measured values to the data store and arranged to read data from the data store during data transmission; an antenna; and a transmitter coupled to the antenna and configured to transmit the stored data by passive transmission.

Preferably the power source is a rechargeable power source and the transmitter is configured to supply at least part of the electromagnetic power received at the antenna to the rechargeable power source so as to recharge the rechargeable power source.

The data logger device may further comprise selector logic, with the transmitter being configured to supply at least part of the electromagnetic power received at the antenna to the rechargeable power source if the selector logic selects that the rechargeable power source is to be recharged. The selector logic may be arranged to select that the rechargeable power source is to be recharged if the voltage across the power source drops below a predetermined level.

At least some of the representations of the measured values may be a difference between a previously measured value and a subsequently measured value of a physical parameter.

Preferably the control logic is arranged to write at least some of the representations of measured values to the data store in conjunction with a timestamp indicating the time at which the respective measurement(s) were taken. Preferably each sensor is configured to measure the one or more physical parameters at a predetermined frequency.

Preferably the control logic has a first mode of operation in which it is operable to write representations of measured values to the data store and a second mode of operation in which it is not operable to write representations of measured values to the data store, the control logic consuming more power in the first mode than in the second mode, and the control logic being configured to enter the second mode of operation when one or more of the following conditions is met:
 (a) a predetermined length of time elapses after writing to the data store;
 (b) when the measured value of a selected one of the one or more physical parameters changes between measurements by more or less than a predetermined amount;
 (c) when the measured value of a selected one of the one or more physical parameters is a value greater than or less than a predetermined value.

Preferably the control logic is configured to enter the first mode a predetermined length of time after entering the second mode. Preferably the data logger further includes comparison circuitry configured to determine when the measured value of a selected one of the one or more physical parameters changes between measurements by more or less than a predetermined amount, and the comparison circuitry being arranged to, in response to this determination, cause the control logic to enter the first mode and write representations of at least some of the measured values to the data store.

Preferably the data logger further comprises means for averaging a set of measured values of a selected one of the one or more physical parameters and causing the control logic to write a representation of the average of the set of measured values to the data store.

The physical parameters may be one or more of temperature, pressure, pH, light intensity, acoustic pressure, movement, light spectral quality, orientation or tilt of the data logger, and vibration.

Preferably the data store of the data logger is arranged to store additional data. The additional data may include personal and/or medical information.

At least some of the one or more physical parameters may be physiological parameters and the data logger device may be incorporated into one of:
 (a) a package suitable for implantation in an animal or human body;
 (b) an adhesive patch suitable for wearing on the skin; and
 (c) an item of clothing or other wearable item;
 (d) a protective shell.

One of the one or more sensors may be a first temperature sensor. One of the one or more sensors may be a second temperature sensor, and the first temperature sensor is arranged to measure the temperature of a human or animal body and the second temperature sensor is arranged to measure the ambient temperature of the human or animal body.

One of the one or more sensors may be an accelerometer or other means for measuring movement of the data logger device or the body to which the accelerometer or other means for measuring movement is attached.

Preferably the control logic is arranged to write a representation of a measured value of a first selected one of the one or more physical parameters to the data store only when the variation in previously measured values of a second selected one of the one or more physical parameters is less than a predetermined value.

Preferably the control logic is arranged to write a representation of a measured value of a selected one of the one or more physical parameters to the data store only when the measured value changes between measurements by more than a predetermined amount.

The representation may be a timestamp indicating the time at which the change was measured.

According to a second aspect of the present invention there is provided a system for in-situ measurement of one or more physical parameters comprising: a data logger device as claimed in any preceding claim; and a data reader device comprising a receiver configured to receive at least some of the stored data from the data logger device by passive transmission.

Preferably the data logger is configured to transmit at least some of its stored data when the energy received by the receiver from the data reader exceeds a predetermined level.

Preferably the data logger is configured to transmit at least some of its stored data in response to an appropriate command from the data reader. Preferably the command indicates which of the stored data the data logger is to transmit.

Preferably each sensor is configured to measure the one or more physical parameters at a predetermined frequency and the data reader is operable to transmit a signal to the data logger to set this frequency.

Preferably the data store of the data logger is arranged to store additional data. The additional data may include personal and/or medical information. Preferably the data logger is configured to transmit at least some of the additional data upon receiving an appropriate command from the data reader.

Preferably in response to receiving an appropriate command from the data reader, the data logger is configured to (a) overwrite at least some of the additional data with data transmitted in conjunction with the command, or (b) write data transmitted in conjunction with the command to the data store as further additional data.

Preferably the data reader is operable to transmit an authentication code to the data logger. At least part of the authentication code may be determined in dependence on an identification code of the data logger. At least part of the authentication code may be determined in dependence on an identification code of the data reader. Alternatively the data logger holds a set of valid authentication codes and the data logger is configured to transmit at least some of its stored data to the data reader only if it receives a valid authentication code.

Preferably the data logger is configured to perform public key authentication of the data reader, or vice versa, and the data logger is configured to transmit at least some of its stored data to the data reader only if it receives a valid response.

Preferably the data reader device comprises input means for inputting data into the reader. Preferably the data reader device is configured to store at least some of the data received at the data reader device.

The data reader device may be operable to transmit by wired or wireless communication at least some of the data received from the data logger to one or more of an internet server, a personal computer (which includes a laptop, desktop, PDA, smartphone or handheld computer), a storage device, or any other data processing device.

Preferably the data reader device is configured to process each measured value of the first temperature sensor in dependence on the corresponding measured value of the second temperature sensor so as to form an estimate of the core body temperature of the human or animal body which the first temperature sensor is arranged to measure.

Preferably the data reader device is configured to disregard at least some of the measured values of the first temperature sensor which were measured when the variation in measured values of the accelerometer or other means for measuring movement exceeded a predetermined value.

Preferably the data reader device is configured to disregard at least some of the measured values of the first temperature sensor which were measured when the measured values of the accelerometer or other means for measuring movement exceeded a predetermined value.

According to a third aspect of the present invention there is provided a system for determining the point of ovulation in a female comprising: a data logger device comprising: a first temperature sensor for measuring a first temperature of the female; a data store for storing one or more first temperature measurements as a first physiological data set; control logic configured to store representations of first temperature measurements at the data store; a transmitter configured to transmit at least some of the stored data; a data reader device comprising: a receiver configured to receive at least some of the stored data from the data logger device; and a data processor having input means operable to receive at least one other physiological data set; wherein the data processor is arranged to combine the first temperature data from the data reader device and the at least one other physiological data set so as to form an indication of the point of ovulation.

Preferably the data logger device is incorporated into one of:
(a) a package suitable for implantation in an animal or human body;
(b) an adhesive patch suitable for wearing on the skin; and
(c) an item of clothing or other wearable item;
(d) a protective shell.

The at least one other physiological data set may include at least one of cervical fluid quality data, hormone level data, and data indicating dates of at least one previous menstruation.

Preferably the data processor is operable to combine the first temperature data and the at least one other physiological data set by means of an ovulation prediction algorithm which is configured to assign a different statistical weight to each of the data sets. The statistical weights may be based upon the degree of previous correlation between the point of ovulation indicated by the data sets and the actual point of ovulation.

Preferably the data processor or data reader is operable to prompt the user to provide additional physiological data sets at the input means of the data processor.

The data reader device preferably comprises a housing and the data processor may be incorporated within the housing of the data reader device. Preferably the data reader device is a hand-held device.

Preferably the data reader device includes a memory for storing the data received from the data logger device. Preferably the data reader device includes a display for displaying the data received from the data logger device. Preferably the data reader device is arranged to make available by wired or wireless communication with the data processor at least some of the data received from the data logger.

Preferably the data logger device further comprises an accelerometer or other means for measuring movement of the female and the control logic is further configured to store representations of the movement measurements at the data store, the data processor being operable to disregard at least some of the temperature measurements which were measured when one of the following conditions was true:

(a) the variation in the movement measurements exceeded a predetermined value;
(b) the movement measurements exceeded a predetermined value.

Preferably the data logger device further comprises an accelerometer or other means for measuring movement of the female and the control logic is further configured to not store at least some of the representations of the first temperature measurements at the data store when one of the following conditions is true:
(a) the variation in previous movement measurements exceeds a predetermined value;
(b) at least one previous movement measurement exceeds a predetermined value.

Preferably the at least one other physiological data sets received at the input means of the data processor is movement data for the female and the data processor is operable to disregard at least some of the first temperature measurements which were measured when one of the following conditions was true:
(a) the variation in the measurements represented by the movement data exceeded a predetermined value;
(b) the measurements represented by the movement data exceeded a predetermined value.

Preferably the data logger device further comprises a second temperature sensor and the control logic is further configured to store representations of the second temperature measurements at the data store. Preferably the second temperature sensor is arranged to measure the ambient temperature of the female and the data reader device is configured to process each measurement of the first temperature sensor in dependence on the corresponding measurement of the second temperature sensor so as to form an estimate of the core body temperature of the female.

Preferably the data processor is operable to make a first determination in dependence on the data from the data logger and/or the at least one other physiological data sets as to whether the female has reached a basal body temperature and, if the outcome of the first determination is negative, the data processor is configured to form an estimate of the basal body temperature in dependence on at least one of the following:
(a) a rate of change in any of the temperature measurements;
(b) a rate of change in the rate of change in any of the temperature measurements;
(c) data representing previous variations in temperature as the temperature of the female approached a basal body temperature.

Preferably the data logger is arranged to transmit at least some of its stored data to the data reader by wired or wireless transmission.

According to a fourth aspect of the present invention there is provided a package comprising a data logger device, the data logger device including: a first temperature sensor for measuring a first temperature; a data store for storing one or more first temperature measurements; control logic configured to store representations of first temperature measurements at the data store; and a transmitter configured to transmit at least some of the stored data; and the package further comprising first and second portions, the data logger device being held therebetween; wherein the first temperature sensor is adjacent to the first portion and at least a region of the first portion proximate to the first temperature sensor has a higher thermal conductivity than the second portion.

Preferably the face of the first portion opposed to the data logger supports a layer of adhesive so as to allow the package to be affixed to an object or the body of a human or animal such that the first temperature sensor is proximal to the object or body.

Optionally the package further comprises a band or strap arrangement configured so as to fit about a part of an object or human or animal body and, in use, to hold the package to the object or human or animal body such that the first temperature sensor is proximal to the object or body.

Preferably the first portion has an opening located so as to expose the first temperature sensor of the data logger device.

Preferably the first portion has an opening through which the data logger device may be inserted or removed.

Optionally the first and second portions of the package are disposable.

Preferably the data logger device further includes a power source and the first temperature sensor is mounted against the power source.

Preferably the data logger device further includes a second temperature sensor for measuring a second temperature. Preferably the second temperature is the ambient temperature of the package. Preferably the second portion has an opening located so as to expose the second temperature sensor of the data logger device.

The present invention will now be described by way of example.

Figure 1:
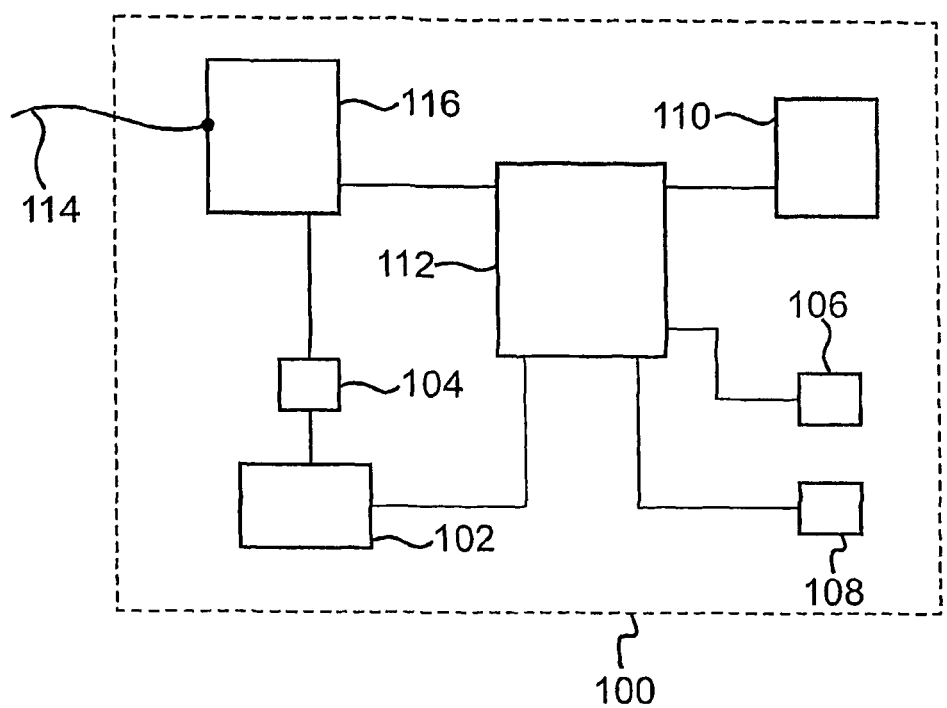
FIG. 1 is a schematic diagram of a data logger device.

FIG. 1 is a schematic diagram of a data logger device 100 in accordance with the present invention. In the data logger device of FIG. 1, control logic 112 samples the signals from one or more sensors 106 and stores the result in the data store 110. In the preferred embodiment the control logic includes an analogue-to-digital (A-D) converter that converts the analogue signals from sensors 106, 108 to digital values for storage in data store 110. Control logic 112 further includes a timer to allow periodic storage of the sensor values at regular intervals. At least part of the control logic for sensing or storing a sensed temperature is powered by power source 102.

Transceiver 116 is operable to transmit data stored in data store 110. In order to minimise the drain on power source 102, in a preferred embodiment, any logic necessary for data transmission draws its power from an electromagnetic field coupled to antenna 114, to which the transceiver is connected. Antenna 114 is preferably a wire coil with a core having a high relative permeability, such as ferrite. Data transmission is possible when the transceiver is coupled to an appropriate oscillating electromagnetic field, such as may be provided by a data reader. Data transmission does not therefore require any net power from power source 102.

Figure 2:
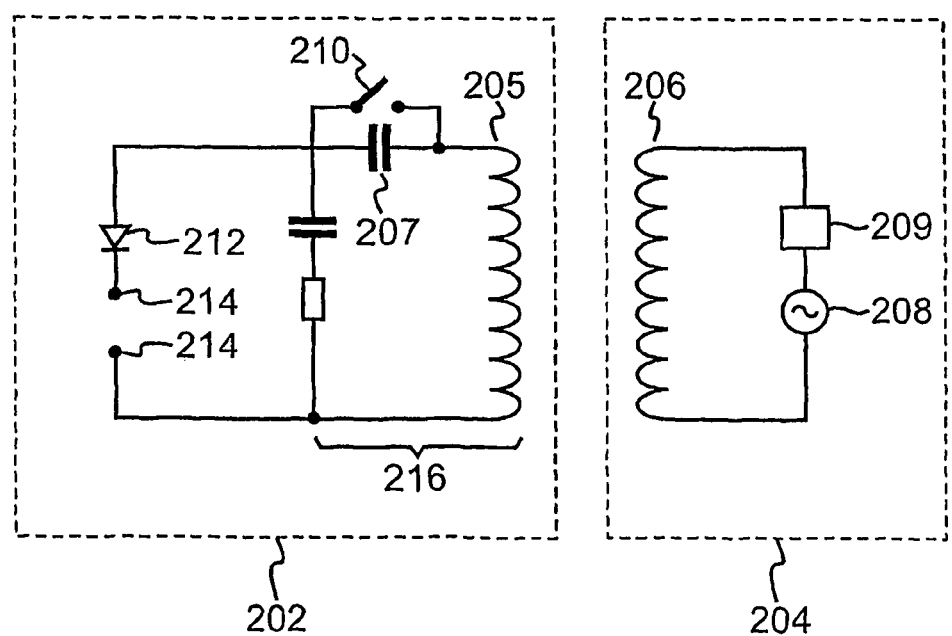
FIG. 2 is a circuit illustrating the passive data transmission principle.

Data transmission in the present invention preferably operates according to the principles set out in FIG. 2. Alternatively, any of the known passive transmission methods known in the art (particularly in relation to passive mode RFID systems) may be employed.

Transceiver 116 can be considered to comprise a transmitter and receiver. Here "transmitter" is taken to mean any element or group of elements that may effect data transmission by any means. "Receiver" is taken to mean any element or group of elements that receives power and/or data from an electromagnetic field to which it is coupled (preferably via an antenna). An element of circuitry may be identifiable as both part of a transmitter and part of a receiver.

In a passive transmission system, power may be transferred in one direction and data in another. FIG. 2 is a circuit illustrating the passive transmission principle employed by many passive mode RFID systems. Typically, a radio frequency signal is generated at the reader 204 by generator 208 which drives reader coil 205. Transponder 202 receives power from reader 204 via electromagnetic coupling between the reader coil 206 and transponder coil 205. The oscillating voltage induced in circuit 216 is rectified by diode 212 to provide a useful voltage between terminals 214. This voltage may be used to drive circuitry.

In particular, the power received at the transponder may be used to drive transmitter circuitry. The transmitter circuitry in FIG. 2 is represented by a switch 210 that shorts out capacitor 207 when closed. By opening and closing switch 210 the resonant frequency of LCR circuit 216 may be switched between two values. This in turn determines the power drawn by circuit 216 from the oscillating field generated by coil 206. It is most straightforward to consider coils 205 and 206 forming a transformer: switching the resonant frequency of circuit 216 switches the load on coil 205. This change in load can be detected at the reader by means of a detection circuit 209, which may be an ammeter. Thus, digital data may be sent from transponder 202 to reader 204 by simply switching between the two resonant states of circuit 216 by means of switch 210. Typically only one of the resonant frequencies of circuit 216 is at or close to the frequency generated by generator 208. This yields a strong change in load at coil 205.

Preferably, power source 102 is rechargeable. Since transceiver 116 is operable to derive power from an oscillating electromagnetic field at the antenna 114, the transceiver may supply power to the rechargeable power source. Furthermore, since the transceiver transmits passively, it requires an incident electromagnetic field from the reader device in order to transmit data to the reader. The reader may provide a field for providing power to the data logger and a separate field to allow passive data transmission via manipulation of the field by the data logger. The data logger may therefore be provided with a second antenna and further transceiver circuitry. Preferably the two fields are one and the same.

Preferably power source 102 is a rechargeable battery. Most rechargeable batteries exhibit a reducing capacity to store charge over a number of recharging cycles. In an application where the battery may be recharged daily, yet needs to have a capacity of months worth of charge, this can have an adverse effect on battery life. It is therefore optimal to recharge the battery only when required, as it reaches a minimum level of charge. However, the data logger described herein need not be able to request a recharge—in this case it must take advantage of recharging when presented. Therefore, to minimise the degradation in battery performance caused by an excessive number of recharge cycles, a protocol based on estimated charge may be used, and/or remaining battery charge as indicated by battery voltage (in loaded and/or unloaded conditions) is proposed.

Selector logic may be provided to select whether or not the power source is to be recharged. The selector logic may allow the power source to be recharged when the voltage across the power source drops below a predetermined level. The predetermined level may be stored at manufacture in the selector logic. Alternatively, the selector logic may allow the power source to be recharged when at least a predetermined time has elapsed since the last recharging. Recharge selection may be effected by switching on or off a current passing element (such as a transistor) under certain conditions as dictated by selector logic.

Figure 3:
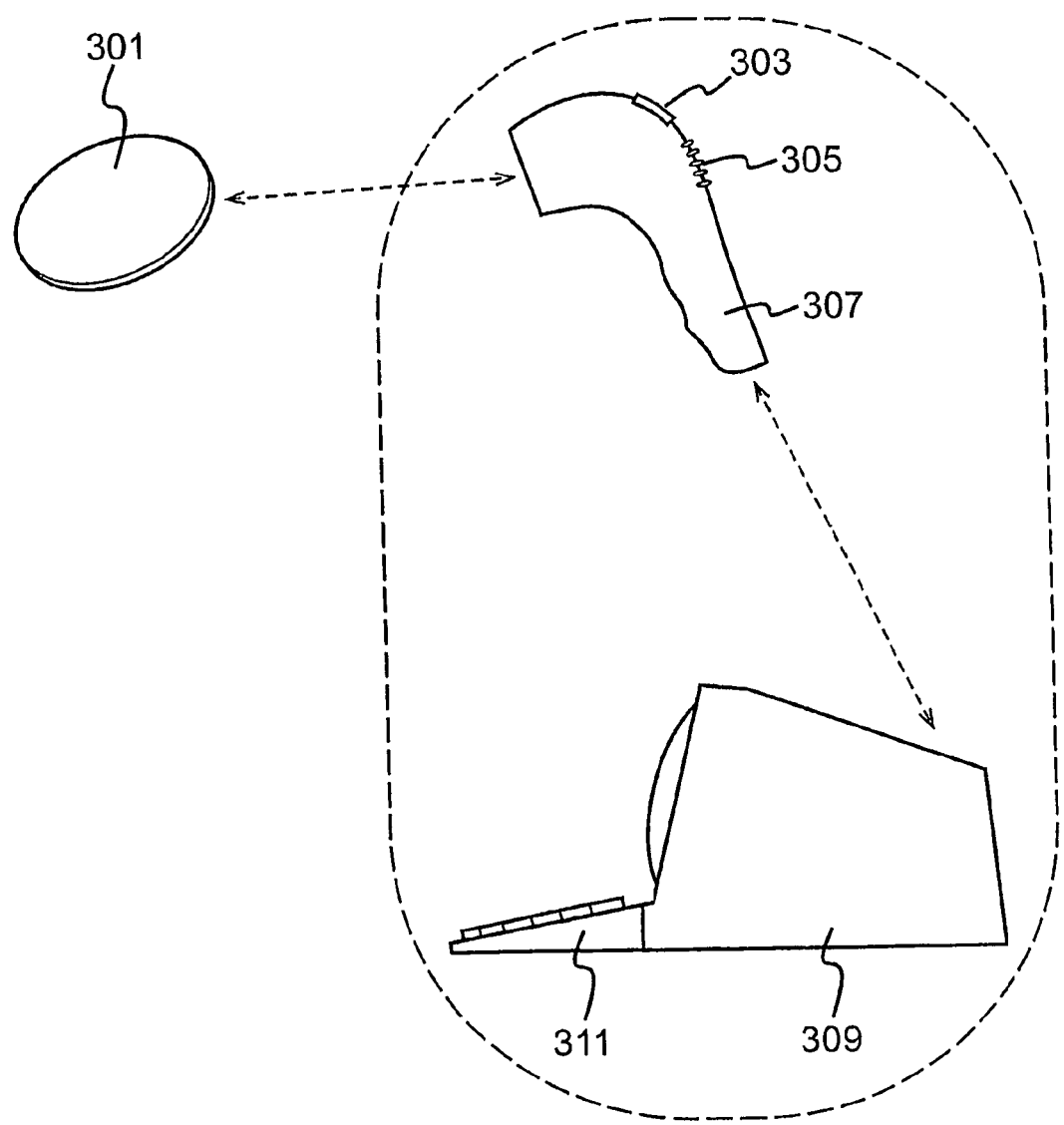
FIG. 3 illustrates the relationship between a data logger, a data reader and a data processor in accordance with an embodiment of the present invention.

In a preferred embodiment, the transceiver receives its power from an oscillating electromagnetic field generated by a reader device. A data logging system in accordance with an embodiment of the present invention is illustrated in FIG. 3. The reader device 307 may be hand held and therefore may be easily positioned by the user so as to arrange efficient coupling between the reader device and data logger device 301. The reader may include a screen 303 to enable viewing of the received data or to provide a visual menu interface to the user. The reader may be battery powered or may be physically connected to a second device, such as a processor device 309 for processing the received data. The data may be sent from the reader to a data processor wirelessly or by wired communication. Alternatively, the data processor may form part of the data reader.

The reader may include one or more inputs, such as a keypad 305, via which the user may interact with the reader or input data into the reader. The data processor may include one or more inputs 311, allowing the input of further data sets to the data processor or to allow interaction with the functionalities of the data processor/reader. As indicated by the dotted border in FIG. 3, the data reader and data processor may form part of the same device, or they may be separate devices.

The data logger may further comprise receiver logic to interpret one or more commands received at the transceiver and encoded into the electromagnetic field provided by the reader. The data may be sent to the data logger by switching the frequency or amplitude of the electromagnetic field, or by any other transmission techniques known in the art. Preferably the receiver logic is also powered by the power drawn by the transceiver from the electromagnetic field.

The reader may send one or more commands to the data logger. These may include commands to set the sampling interval of sensors 106, a command to initiate data transfer, and also configuration commands, such as calibration constants, ID codes, reset commands and updates for any control logic implemented as firmware.

Alternatively, calibration factors, sampling interval and logger ID are fixed during manufacture.

In one embodiment the transceiver starts transmitting the stored data once the power received at the transceiver exceeds a predetermined level. Alternatively, the transceiver starts transmitting when a signal is received from the reader. Preferably the reader transmits an identifier to the data logger which includes an identification code. The data logger will only transmit the stored data to the reader if the identification code matches a code stored at the data logger. The data logger may (a) store one or more identification codes corresponding to one or more data readers or (b) the data reader may be required to transmit the data logger's unique code. The identification code(s) may be stored in data store 110. Preferably the data logger does not transmit its code and thus in case (b) the reader is required to have prior knowledge of the code. This helps protect the data stored at the data logger from unauthorised or unwanted viewing. Alternatively, the use of known cryptographic protocols may be used to provide enhanced security, such as "challenge-response" protocols, or others known in the art.

The data logger may store data in data store 110 other than the sampled sensor signals. This may include one or more identification codes as discussed above, and/or data relating to the user, such as personal identification information or medical information. This is particularly useful in the case that the user is a patient and the data logger is being used to log physiological parameters of a patient: the medical information could be general patient identification information or the results from previous medical tests or observation notes. This other data may also be sent to the reader.

A reader may be required to provide different identifiers in order to receive the different data types. For example, a first identifier may be required to trigger the data logger to transmit the stored physiological parameter data and a second identifier may be required to trigger the data logger to transmit the user/patient information.

The data store 110 is preferably a non-volatile memory, such as a battery-powered RAM, EEPROM, FLASH RAM, or more preferably FRAM or MRAM. Power source 102 may be a capacitor or battery.

In one embodiment, at least one of the sensors is a temperature sensor. Preferably the temperature sensor is a thermistor. Alternatively, the temperature sensor may be a silicon based device, such as a "proportional to absolute temperature" voltage source. To increase sensitivity the signal may be boosted by signal conditioning elements, such as bridges, filters, and amplifiers.

In order to minimise the size and power requirements of the data logger, where possible the data logger circuitry is fabricated as a single microchip.

In the case of a data logger device for measuring one or more physiological parameters, the device may be provided as a (sub-dermal) implant or as a wearable patch. As an implant the data logger housing is preferably inert and coated to help prevent rejection by the immune system of the host.

Examples of the physical parameters that may be measured by a data logger are temperature, pressure, pH, light intensity, vibration, acoustic pressure, orientation or movement. Examples of the physiological parameters that may be measured by a data logger are body temperature, blood pH, blood glucose, pulse rate, blood pressure. These parameters may be measured by any of the methods known in the art.

A data logger device in accordance with the present invention may be configured to measure body temperature so as to allow automated determination of basal body temperature. This allows the point of ovulation to be estimated from one ovulation cycle to the next by looking for a rise in the basal (minimum resting) temperature over a number of days. This is substantially independent of the short term variations in skin temperature of the user, which can vary rapidly throughout each day as a result of changes in activity level, environmental temperature etc.

Since body temperature typically varies slowly, several improvements can be made to the data logging process. A first improvement is to compress the sensor data at the data logger. A data stream of the differences between the previous and current measured temperature is a good candidate for "entropy encoding" or any other means of minimising the memory requirement for values that occur frequently compared with values that occur less frequently. This allows a greater number of measurements to be stored at the data logger.

By using an appropriate compression scheme, for example Fibonacci coding, it is possible to separate individual data points. Data can be simply read from a circular buffer with an error introduced in only the last two measurements in the memory, which can be easily discarded.

Data that is not recorded at a fixed interval may require that a record (e.g. a timestamp) is kept of when data (or groups of data) were measured. For example, if the memory becomes full, old values can be replaced with new values and a timestamp ensures that it is known when each sensor value was measured.

A second improvement is to only record a timestamp when the temperature changes by more than a predetermined amount (e.g. 0.01 degrees) from the last measured value. Measurements can be taken at a predetermined frequency or the sensors can be essentially continuously monitored for changes in temperature. The temperature value or difference may or may not be recorded with the timestamp. By recording differences in time the data is amenable to compression, as described above.

Often rapid small fluctuations in sensor values are unimportant, such as in temperature measurements to determine the point of ovulation. In such cases a very simple A/D converter or sample-and-hold circuit can be used for performing the comparison of temperature values in order to determine the difference between the last and current values. A main A/D converter may be held in a sleep state until the difference is larger than a predetermined amount and the timestamp and/or the temperature value is to be stored at the data logger. This scheme could be further augmented with a minimum sleep time so as to avoid the main A/D converter being awoken too often during periods of large rapid temperature fluctuations. These schemes help save both memory and power at the data logger.

A third improvement is to average values over time. This has the effect of discarding information about rapid fluctuations in the sensor values, essentially removing high-frequency "noise". This can be achieved through the use of a sliding window: for example, a circular buffer could hold the last 16 measurements, measured at 14-bit resolution, and a 16-bit average of the measurements would be stored in memory. The sum of these 14-bit measurements is an 18-bit number but, assuming a Gaussian noise distribution in the least significant bits of the A/D signal, an improvement in signal:noise of sqrt(16)=4 would be produced: using only the top 16-bits of the 18-bit number yields a 16-bit value from the 14-bit measurements. Other bit lengths and buffer sizes could be used.

A further improvement would be to not include the maximum and minimum measurements in the buffer in the averaging calculation. This helps to minimise the effect of outlying measurements. Some number of measurements could also be selectively excluded, for example only the middle 12 measurements of 16, to further reduce the effect of brief periods of outlying measurements.

Natural Family Planning works by monitoring certain physical signs that occur during the menstrual cycle. The most common signs that are observed are menstrual bleeding, cervical mucus changes and body temperature changes.

The calendar rhythm method is the oldest and most widely practiced of the fertility awareness methods. Calendar charting allows women to estimate the onset and duration of the time when an egg is available for fertilization by the sperm. Calculation of the fertile period is made from three assumptions: 1) ovulation occurs on day 14 (plus or minus two days) before the onset of the next period; 2) sperm survive for two to three days; 3) the ovum, or egg, survives for 24 hours.

The basal body temperature (BBT) method is commonly employed by taking an oral temperature first thing in the morning, preferably at the same time every morning, and plotting these temperatures on a chart. Ovulation is generally indicated as having occurred after three consecutive days where the temperature is higher than any of the previous 7 days. Using this method, ovulation cannot be predicted but can be identified once it has occurred. This method is most useful for identifying when the woman's infertile time has started.

Cervical mucus changes have a distinctive pattern among most ovulating women, even those whose cycles are irregular. To evaluate cervical mucus, a woman obtains some mucus from her vaginal opening. In checking her mucus, a woman needs to determine if it feels wet or dry. Mucus qualities such as tackiness, elasticity and wetness suggest where she is in her cycle. Release of the egg usually happens the day before or during the last "slippery, wet" mucus day. The fertile time occurs when the mucus has the characteristics of uncooked egg white. Use of vaginal lubricants or douching can make these characteristics more difficult to recognize.

The various charting methods may be used alone or in combination. A common technique is for women to record changes in their mucus and to record their basal body temperature. Some women also notice and record ovulatory pain which can include feelings of heaviness, abdominal swelling, rectal pain or discomfort and lower abdominal pain or discomfort. Pain can occur just before, during or after ovulation.

The data logger described herein can perform the temperature monitoring aspect automatically, whereas the woman would need to keep a record of the other subjective parameters such as mucus changes herself. By inputting these additional subjective parameters into the a reader device (as described above) or into a data processor to which the temperature data is sent, and making use of it only when available (although not requiring it to be available), it can be selectively combined with the temperature data and time/date data to estimate future dates for ovulation, and also the future dates for expected changes in the subjective parameters, prompting the woman to monitor them when it is most likely that they are needed.

The importance of these additional subjective parameters is that temperature rises AFTER ovulation, whereas other subjective parameters change BEFORE ovulation. If one tries to identify the fertile window only using temperature, the window of uncertainty is wider because the post-ovulation part of the cycle is well defined (typically 10-12 days or so prior to menstruation), and does not vary much in length from cycle to cycle. Hence temperature logging can identify this period. However, the pre-ovulation part of the cycle is of variable length cycle-to-cycle. By adding in data about the first day of menstruation, a second quite objective parameter has been added and the estimation of the timing of ovulation can be improved.

By adding in information about quality of cervical mucus, for example, the onset of the fertile window can be determined more accurately. However, the quality of cervical mucus is very hard to establish reliably for some women, particularly after intercourse in the preceding day. It is most beneficial if further physiological data is used only when provided, and the system relies on temperature measurements and timing to calculate the onset of the fertile window when not provided. Similarly other parameters such as saliva quality, breast tenderness, ovulatory pains, and hormone measurements can all be added in if observed.

A data logger device for monitoring body temperature may take the form of an implant that is injected into the female or inserted in a minor operation. The data logger is preferably inserted into the abdomen or inner upper arm so that the temperature logged by the data logger is an accurate reflection of the true core body temperature. Alternatively the data logger can be incorporated into a patch, wearable band or an item of clothing (such as underwear). This implementation is described below.

Figure 6:
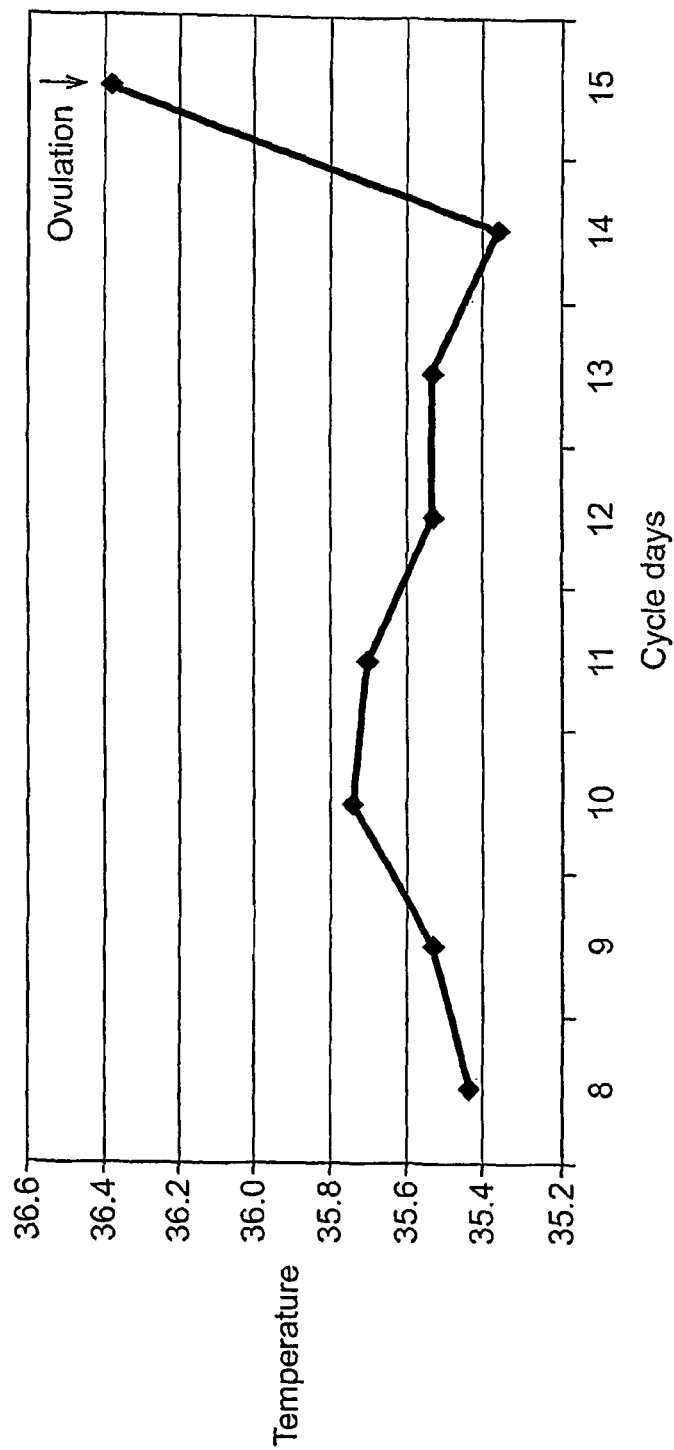
FIG. 6 shows (i) a plot of BBT as estimated by a prototype data logger in accordance with an embodiment of the present invention and (ii) a plot of the mean of two body temperature measurements taken at 6.30 am with a Braun ThermoScan.

FIG. 6 illustrates the benefit of using a temperature data logger to estimate basal body temperature. The first plot in FIG. 6 is of daily basal body temperature as estimated from data periodically logged overnight while the user was asleep by a prototype data logger in accordance with an embodiment of the present invention. Temperature measurements taken during periods of high movement were ignored and the remaining temperature data from the data logger was processed to remove outlying temperature measurements. An average of the then remaining temperature measurements was taken to eliminate short-term fluctuations in measured temperature.

The second plot is of body basal temperature over the same days as the first plot estimated using a conventional technique: two measurements were taken by the user with an aural thermometer (a Braun ThermoScope) at 6.30 am upon waking. The prototype data logger clearly detects the date of ovulation (indicated by the arrows in the plots) whereas it is very difficult to detect using the conventional approach. Use of a data logger also removes the need for the user to wake early each morning, take their temperature and note it in a log book.

Figure 7:
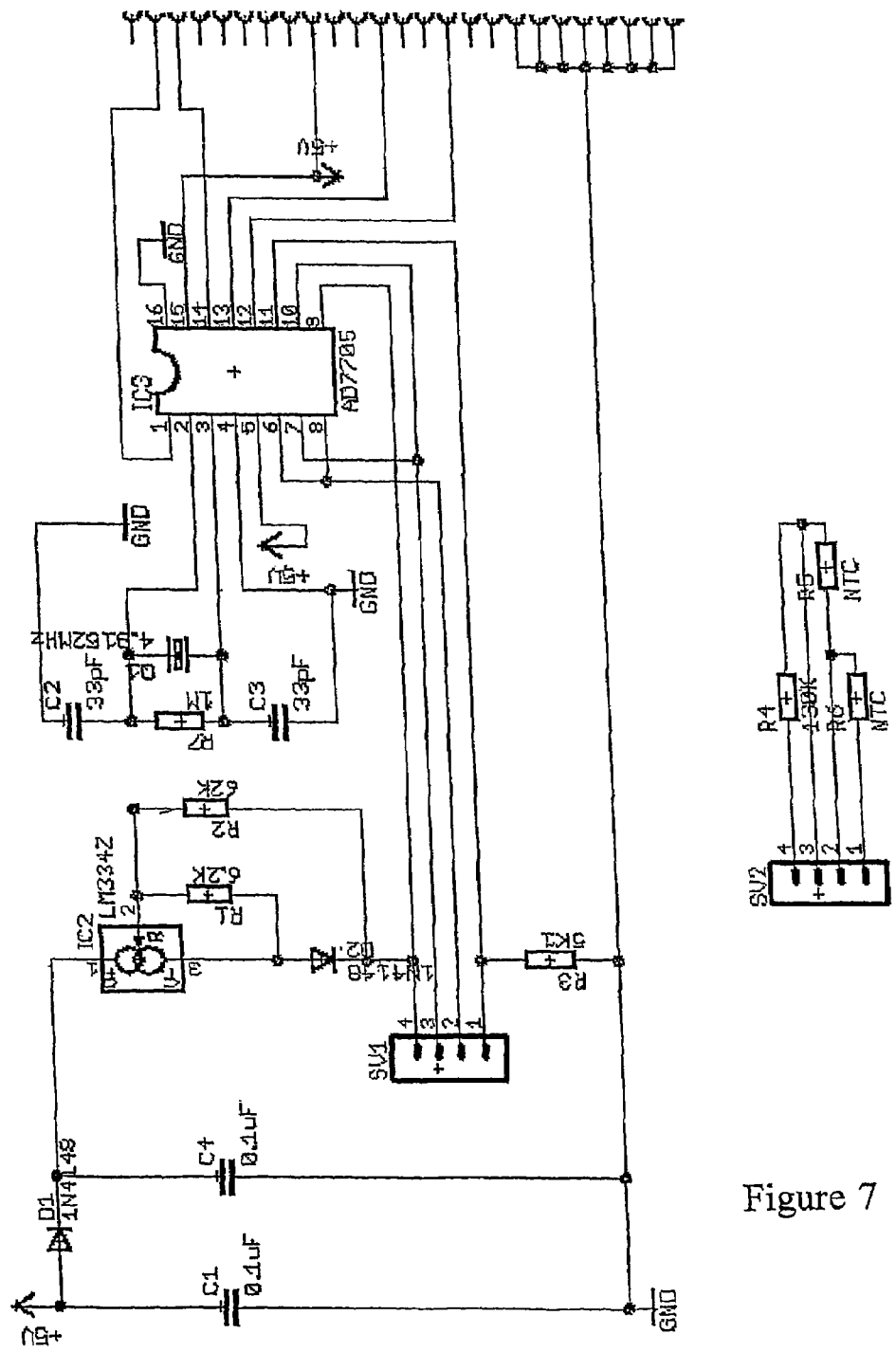
FIG. 7 is a circuit diagram of a prototype data logger in accordance with an embodiment of the present invention.

FIG. 7 shows a circuit diagram of the prototype data logger used to collect the data shown in FIG. 6.

By arranging for the regular read-out of data from the data logger (so as to predict ovulation) the power source is recharged regularly from the power derived from the electromagnetic field generated by the reader. The power source for the device can therefore be relatively small. This combination of small size of the device and wireless recharging during data transmission allows a practical implementation of the device as an implant, or alternatively allows the device to be discretely incorporated into a small adhesive patch which can be affixed to the skin in the same way as a regular sticking plaster or band-aid.

In one embodiment, the data logger includes an integrated circuit containing control logic, timing, measurement, power control, temperature sensing, and wireless communications, which is bonded to a lithium polymer battery for power storage, and the antenna. Because the data logger measures body temperature, the temperature range that the device is exposed to is very narrow and so very low power analogue timing for the sampling frequency is possible with acceptable accuracy using R-C time constants. The change in the power supply over time can also be measured periodically and thus the frequency of measurement can be calibrated during logging. Typically the data logger logs temperature at a predetermined frequency (e.g. every 10 minutes), and records this in memory.

The system for determining the point of ovulation may comprise a data logger in any of its forms described herein and which is configured to measure temperature, a data reader in any of its forms described herein and a data processor. Alternatively the data logger may be any temperature data logger known in the art capable of passive transmission and with which the data reader is compatible. The data logger transmits its stored data to the data reader by passive transmission. The data reader and data processor may communicate by any means known in the art.

The reader device may have a display and user input capability so as to allow the user to view tables or graphs of the data received from the data logger, and/or to allow the user to interact with graphical menu systems. The reader device may be connected to a data processor or the data processor may form part of the reader device. It is only important that there is some aspect of the system which is capable of processing the data received from the data logger so as to provide an indication of the point of ovulation in the female user. The data processor may simply be a personal computer supporting software arranged to perform the data processing.

Either the data reader or data processor includes input means for inputting at least one other set of physiological data for the female user. The data processor can combine the temperature data with the other sets of physiological data (such as quality of cervical mucus, hormone test results from blood or urine etc) to provide an indication of the point of ovulation in accordance with any of the principles of ovulation detection described above or known in the art.

Preferably the reader device consists of a portable wireless reader with two-way communication with the implant when activated in suitable proximity. The user interface may include a number of buttons, to input such data as menstruation days and cervical fluid quality, and a simple LCD display prompting for measurements or indicating parameters such as implant and reader battery charge. Equally, the user may input any further physiological data directly into the data processor if the data processor is arranged to receive such inputs—this would be convenient for the user if the data processor is a personal computer. The reader itself may be capable of estimating the point of ovulation based upon previously recorded data (which may be stored at the reader and/or at the data processor), and is suitably capable of displaying the expected number of days of until the next ovulation to the user. For privacy reasons, the device will preferably not display any information on fertility unless it has recently been in contact with the implant that it is keyed to.

The reader device may contain a USB port (or other suitable form of wired or wireless connectivity) to allow connection to a personal computer. This allows for (a) recharging of the internal battery of the reader, and/or (b) data transmission to and from the computer for data storage, further processing of the data, data display or simply because the computer performs the temperature data processing in the system. When the reader or data processor finds data that does not fit an expected model of ovulation, or needs additional user interaction, it can prompt the user to connect it to a personal computer.

The device may appear to the computer as a USB "drive" storage device, with the software and manuals for the device available on the drive, thus removing the need for separate software (e.g. CDs) to be carried with the device. The software can provide a more extensive user interface, which may be operable to connect to the internet to perform software and firmware updates. Optionally, the user's data can be uploaded over the internet for analysis by third parties, for example medical practitioners.

The computer interfacing aspect of the reader allows the system to act as a training system for the user in the measurement of more subjective physiological parameters, such as quality of cervical fluid, as the training software can incorporate the thermal history and other data of the user. This reduces the user's reliance on physical teaching by a third party, which is frequently considered invasive or embarrassing.

As the user becomes more adept at measuring these additional parameters, the statistical model for ovulation prediction is altered to provide more weighting to these observations. This allows a progressive reduction in the "safety window" around the period of ovulation, during which abstinence should be practiced in order to prevent pregnancy.

Figure 4:
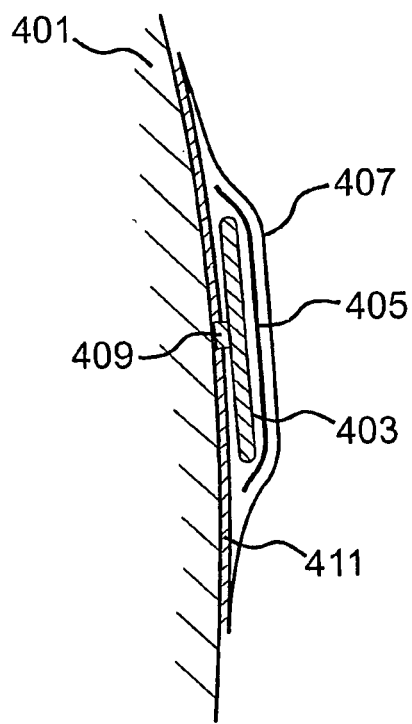
FIG. 4 is a representation of a data logger incorporated into an adhesive patch.
Figure 5:
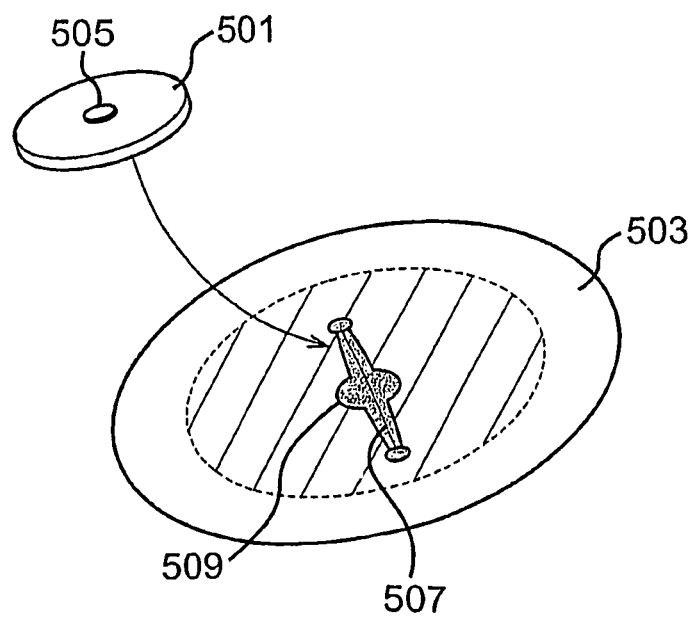
FIG. 5 is a representation of a data logger and disposable adhesive patch.

The data logger described herein may be a human or animal body temperature data logger incorporated into an adhesive wearable patch 407, 503 as shown in FIGS. 4 and 5. The adhesive 411 may be selected from any of the known skin adhesives and is preferably hypoallergenic so as to minimise the risk of an adverse reaction with the skin 401 of the user. The patch preferably holds the data logger 403, 501 in a pouch arrangement which allows the data logger to be removed and installed in a new patch when advantageous—for example, when the adhesive loses its stickiness or the user desires a fresh patch. FIG. 5 shows an opening 507 through which a data logger 501 may be removed and installed. Alternatively the data logger could be sealed in the patch, which can be convenient if the patch and data logger are disposable.

In a preferred embodiment the patch is roughly circular, approximately 2 cm in diameter and skin-coloured. To thermally insulate the body temperature sensor from environmental changes in temperature, the patch may have a thermally insulating region 405 (such as a soft foam backing) that extends over the part of the data logger which is opposite to the side of the data logger held against the body. The patch may have an opening 509 through which a thermally conducting stud 409, 505 of a data logger may protrude and make physical contact with a body to which the patch is affixed. In FIG. 5 this forms part of the opening 507 through which a data logger may be inserted into the patch.

If the data logger does not have a thermally conducting stud, it is generally desirable that the patch (and possibly the data logger shell) is more thermally conductive in the region between the body temperature sensor and the body itself than elsewhere over the patch/shell. This may be achieved through the choice of materials used in the patch/shell and/or by fabricating the patch/shell so the material is thinner in the region over the temperature sensor.

The patch constructions described above may conveniently be supplied as a sterile, disposable device.

Alternatively the data logger may be incorporated into a band (such as may be worn around the arm) or item of clothing, or the data logger may be held in position by an arrangement of straps or bands. The band would preferably be worn around the upper arm with the temperature sensor located on the inside of the arm, adjacent to the armpit. In order to be able to precisely measure small variations in body temperature it is particularly important that the data logger is repositioned at the same location (the measurement spot) on the user's body each time the user refits the band. The band may therefore have markings so as to aid the user in correctly positioning the data logger held within the band. Neoprene, which is comfortable to wear for long periods and is a good thermal insulator is a particularly suitable material for the band.

Several temperature sensors may be held in a ring in the band. This can help to mitigate the effects of poor rotational positioning of the band by the user. Typically there will be a known variation in temperature around the arm (say) about which the band is worn. This variation can be measured and stored as a profile for the particular user at the data logger, or more preferably at the data processor to which the temperature measurements are sent for processing. The profile allows the temperature measurements from each of the sensors to be later correlated with their position about the arm so as to determine which sensor is closest to the "measurement spot". It may be further desirable to use the known temperature profile to interpolate between temperature measurements in order to more precisely determine the temperature at the measurement spot each time the band is replaced. These calculations can be performed at the data processor.

In the embodiments illustrated in FIGS. 3, 4 and 5 the temperature sensors and aerial are incorporated into the main body of the data logger itself. In this embodiment there may be thermally conductive portion(s) of the data logger shell over the temperature sensor(s), or there may be thermally conductive stud(s) coupling the temperature sensor(s) to the body, as shown. However, the temperature sensor(s) may be external to the main body of the data logger and wired to the data logger. Likewise, the aerial(s) may be external to the main body of the data logger—perhaps to improve data and power transfer. The temperature sensor(s) and/or aerials may be integral to the patch/band and connected to the data logger by wires.

Preferably the data logger itself is encapsulated in a sealed shell to protect the components of the data logger from knocks, liquids and corrosion. To allow devices to be re-used by different users, it is also advantageous if the data logger can be sterilized in an autoclave. Preferably the shell has an outer layer of silicone, or another inert material. The silicone may be of variable thickness over the shell such that there is a thinner layer of silicone (perhaps 0.1 mm) over the temperature sensor and a thicker layer of silicone (perhaps 0.5 mm) over other areas of the shell. The thicker layer of silicone can help to thermally insulate the sensor. The silicone may be doped with metal particles over the temperature sensor so as to improve the thermal conductivity of the silicone in that region.

The silicone or other protective material may preferably be injection moldable and insert moldable, waterproof and/or biocompatible.

As discussed above, the data logger may have a stud of a highly conductive material (e.g. metal) which protrudes some or all of the way through the data logger shell/silicone so as to improve the thermal coupling between the temperature sensor of the data logger and the body to which it is applied.

In cases where an estimation of core body temperature is required, but measurements are taken at an external point on the body, an improvement over a simple measurement of skin temperature can be made. If the skin temperature is measured under a thermally insulating patch, and the temperature on the external face of the insulator is also measured (i.e. two measurements are taken), an estimation of the difference between the skin temperature and core body temperature is possible. The simplest implementation is to apply a constant factor to the temperature difference between the two sensors, i.e. $T_{core}=T_{skin}+k(T_{skin}-T_{outer})$. A more complicated, but accurate, method is to take into account cases where ambient temperature is higher than as well as lower than skin temperature, and also to make the correction a non-linear function. Such corrections are preferably applied at the data logger so that only the resulting core temperature estimate need be stored at the data logger. Alternatively both sets of temperature data may be stored and the corrections may be applied at the data processor to which the temperature data is sent.

By calibrating such a patch device against core body temperature (as measured by any conventional technique) under a variety of external temperature conditions, a more accurate correction system may be devised. Alternatively, the calibration may be performed in accordance with any of the following methods with the aim of determining the correction function required to yield an approximately constant core body temperature from the data:

1. Applying known thermal gradients across the patch and measuring the response of the two thermometers.
2. Exposing the outer temperature sensor to a range of temperatures while the patch is worn by a user. It is important that the applied temperature varies more rapidly than the body temperature can respond to the changes in temperature.
3. Analysing the temperature measurements during use for natural rapid variations in external temperature compared to the measured skin temperature. This method is preferably performed at the data logger and may be used to continuously adjust the correction function in response to environmental changes.

In one embodiment calibration calculations are performed at a data reader or data processor (to which the reader may be connected) as follows:
1. The data reader transmits a command to the data logger instructing it to enter a calibration mode.
2. A calibration process is initiated and the data logger transmits the temperature data from the temperature sensors in real-time.
3. The data reader or a data processor to which the data reader is connected calculates the correction function.
4. The data reader transmits the parameters of the calibration function to the data logger to be used in extrapolating the core body temperature from the skin and outer temperature sensor values.

Calibration factors may be stored at the data logger (perhaps after being transmitted from the data reader if the calibration calculations are performed at the reader/data processor). The thermal properties—or derivative numbers representing said properties—of the data logger shell and/or the patch/band may be stored at the data logger or data reader/processor for use in processing of measured data. The thermal properties may be determined during a calibration process or may be available if the data logger shell and/or the patch/band use materials having known properties. Knowledge of these properties can, for example, allow the data processor to calculate a theoretical temperature gradient across the data logger and its enclosures which could be used to extrapolate a core body temperature.

For other sensor types, the relevant physical properties will be stored instead: for example, the acoustic or light transmission properties of the enclosures in which the data logger is incorporated may be stored. The calibration principles discussed above apply equally to calibrating measurements of other physical parameters by other types of sensors.

A data logger having a skin temperature sensor and an ambient temperature sensor (or two sensor inputs for two temperature sensors external to the data logger itself) may be incorporated into a patch or band as described above, but with an additional opening or region of increased thermal conductivity over the outer temperature sensor so as to better thermally couple that temperature sensor to the external environment.

A further improvement may be made by utilising three or more temperature sensors located at positions with different thermal parameters, such as local heat capacity and conductivity. For example, if one sensor is on the body side of the device, with low thermal resistance to the body, one sensor is on the external side of the device, with low thermal resistance to the external environment, and one sensor is in the middle of the device, with a comparatively high thermal resistance to either point and a comparatively high local thermal mass, a suitable calibration scheme can be used to provide a more accurate estimate of core temperature. The calibration scheme can be pre-set, or can be based on an empirical or adaptive algorithm.

The data logger configurations described above are not limited to data loggers designed to measure the skin/body temperature of an animal or human and are generally applicable to measuring the temperature or any other physical parameter of any body, whether flora, fauna, machine, rock etc.

It is advantageous in a data logger for a system for determining the point of ovulation in a female that the temperature data from the data logger is combined with data which indicates the activity state of the female, (The term "female" as used in this application refers to both animal and human females.) Particularly with an externally worn data logging patch or band (although it also an issue with an implanted data logger) identifying the drop in body temperature that indicates a lowering of "body basal temperature" is difficult without being able to correlate the temperature data to the activity of the female user.

When the user is awake and moving around the air-flow around the data logger device and over the skin can lower the skin temperature. In contrast, when a user is asleep the data logger tends to be well-insulated and the skin at a warmer temperature (although this is often the best time to take temperature measurements because the core and skin temperatures are stable). And when the user is exercising or has a fever there can be increases in both skin and core body temperature. It is most preferable to measure the body temperature when the user is at rest since this helps to avoid erroneous measurements due to changing temperature conditions unrelated to variations in basal body temperature.

It is advantageous to measure movement, either at the data logger or otherwise, and relate this data to the measured temperature data at the data processor so as to better determine the basal temperature of the user. For example, the basal temperature may be determined from the lowest temperature measured during periods of low movement that last longer than 30 minutes. The motion data may be captured at the data logger itself—for instance, by including an accelerometer in the data logger. In this case, either acceleration/vibration data may be logged or knowledge of the force of gravity can be used to measure the "tilt" of the data logger, as is known in the art. As the user moves, the tilt will change, and so movement can be inferred. Alternatively, any other means of detecting movement could be used, such as a motion-detecting video camera coupled to the data processor, a pulse sensor (which indirectly indicates when the user is moving/exercising), and a sensor in a bed/mattress which detects movement on the bed (e.g. the user rolling over).

Preferably movement of the user is measured at the data logger itself. During periods of high movement the data logger can be set not to log any temperature data. The movement data itself need not therefore be logged at the data logger—it is used to determine when to measure and log temperature and when not to do so. This makes efficient use of the memory at the data logger.

Alternatively, both movement and temperature may be logged at the data logger and the data processor can subsequently combine these data sets in order to determine which portions of temperature data are likely to correlate closely to the true core body temperature of the user and which portions of data are likely to be less reliable. Performing this at the data processor allows a more sophisticated approach to be taken. For example, more complex algorithms can be applied that allow short periods of motion to be overlooked (such as the user rolling over in their sleep) in determining when a relatively extended period of low movement occurred in which good quality temperature measurements are likely to have been taken. Those temperature measurements taken during relatively extended periods of low movement are preferably used in determining the basal body temperature (or some analogue thereof) and the remaining data may be discarded.

A preferred method by which temperature data from a data logger may be processed at a data processor in combination with movement information for the user (from either the data logger or external measurements) will now be described.

1. Identify periods of low movement in the user of duration at least a predetermined length (e.g. 30 minutes).
2. Identify the temperature measurements that correspond in time to the window of low movement.
3. Calculate the mean of those measurements to yield the average resting temperature.

This processing is preferably performed on the data of each day (or night) for which there is data at a time so as to provide an estimate of the daily basal temperature of the user. The temperature data may be limited to those measurements taken when the user is likely to be asleep or at rest by only processing temperature data taken between certain hours (e.g. 11 pm to 6 am). Or the user could simply only wear the data logger (as a patch, arm band etc.) when sleeping.

It has been found that a reliable estimate of basal body temperature can be determined from temperature data taken while the user is sleeping. However, sometimes the user will only be able to sleep for a short period, or sometimes the temperature data is of poor quality for part of the sleep period. In these cases it is possible to estimate the basal body temperature of the user by extrapolating the slow decrease in body temperature that occurs during the sleep of the user so as to form an estimate of the minimum body temperature the user would have reached had they been able to sleep for a sufficient length of time (or had there been temperature data of a good enough quality). This minimum can be estimated using techniques known in the art from the slope of the temperature-time curve: for example, the rate of change of the slop of the curve can be used to anticipate when the body temperature minimum occurs. The estimate can be improved by comparing the incomplete temperature data with temperature-time curves taken during previous sleep periods: for example, knowledge of how long it typically takes for the user's body temperature to reach its minimum can be used to anticipate when that minimum occurs for a given initial temperature and slope of the temperature-time curve.

It is clear from the above discussions that a data logger in accordance with the present invention can have any number of inputs, each of which may be an input from any kind of sensor (such as a temperature sensor, accelerometer). Upon polling by a data reader device the data logger transmits one or more of the sensor data sets. The data logger may transmit the data to the reader in any of a number of ways, including: transmitting only those data sets requested by the reader, transmitting the data sets in a predetermined order, and transmitting the measurements in the order (or reverse order) in which they were taken.

The data logger might have a programmable data logging interval, which is set when the patch is first applied to the patient (by means of a command from the data reader to the data logger, for example). The data logger may then log data at the specified intervals until instructed to stop (or until the battery dies). In some embodiments the data logger stores a timestamp with each measurement, or stores a timestamp each time the data logger (re-)commences logging.

All the embodiments of a data logger described above in relation to a data logger for use in a system for determining the point of ovulation in a female are generally applicable to data logger devices which may have any number of applications and sensor types.

The temperature data stored at a data logger represents a thermal history of the body to which it is attached over time. For some applications, such as determining the point of ovulation in a female (human or animal), it is not necessary to measure body temperature at every point throughout the day. In this case it is convenient for the user for the data logger to be incorporated into a band which is worn about the upper arm, but which may be removed for showering or playing sports. In these cases, the data logger can stop logging when (for example) the temperature drops below a certain level (because the sensor is no longer in contact with the skin), or when a button is pressed on the data logger/armband, or when it receives a command from the data reader device, to give a few examples.

A (possibly disposable) patch configuration is useful in medical applications, when it is important to have complete and uninterrupted temperature measurements of a patient's body temperature. High resolution (both in temperature precision and in frequency of measurement) temperature data is of use in diagnosing a number of medical conditions, for example certain types of infections, hypothermia or pyrexia. Having access to a complete temperature history stored at a data logging device worn by the patient can help a physician to more quickly reach an accurate diagnosis.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A system for determining a point of ovulation in a female, the system comprising:
    a data logger device comprising:
        a first temperature sensor for measuring a first body temperature of the female;
        a data store;
        control logic configured to store at the data store representations of first body temperature measurements of the female as a first physiological data set; and
        a transmitter operable to transmit at least some of the first physiological data set;
    a data reader device comprising a receiver operable to receive at least some of the first physiological data set from the data logger device; and
    a data processor arranged to access the first physiological data set received by the data reader device and to extrapolate a decrease in first body temperature indicated during a sleep period so as to estimate a basal body temperature of the user representative of a minimum body temperature, and thereby forming an indication of the point of ovulation from said estimated basal body temperature.

2. A system as claimed in claim 1, wherein the data logger device is incorporated into one of:
    (a) a package suitable for implantation in an animal or human body;
    (b) an adhesive patch suitable for wearing on the skin;
    (c) an item of clothing or other wearable item; and
    (d) a protective shell.

3. A system as claimed in claim 1, further comprising a second physiological data set that includes at least one of cervical fluid quality data, hormone level data, and data indicating dates of at least one previous menstruation.

4. A system as claimed in claim 3, wherein the data processor is operable to combine the estimated basal body temperature and the second physiological data set by means of an ovulation prediction algorithm which is configured to assign a different statistical weight to each of the data sets.

5. A system as claimed in claim 4, wherein the statistical weights are based upon a degree of previous correlation between a point of ovulation indicated by first and second physiological data sets and an actual point of ovulation.

6. A system as claimed in claim 1, wherein the data processor or data reader is operable to prompt a user to provide a second physiological data set at a user input of the data processor.

7. A system as claimed in claim 1, wherein the data reader device comprises a housing and the data processor is incorporated within the housing of the data reader device.

8. A system as claimed in claim 1, wherein the data reader device is a hand-held device.

9. A system as claimed in claim 1, wherein the data reader device includes a memory for storing the data received from the data logger device.

10. A system as claimed in claim 1, wherein the data reader device includes a display for displaying the data received from the data logger device.

11. A system as claimed in claim 1, wherein the data reader device is operable to transmit to the data processor by wired or wireless communication at least some of the data received from the data logger.

12. A system as claimed in claim 1, wherein the data logger device further comprises an accelerometer or other means for measuring movement of the female and the control logic is further configured to store representations of the movement measurements at the data store, the data processor being operable to disregard at least some of the temperature measurements which were measured when one of the following conditions was true:
 (a) variation in the movement measurements exceeded a predetermined value;
 (b) the movement measurements exceeded a predetermined value.

13. A system as claimed in claim 1, wherein the data logger device further comprises an accelerometer or other means for measuring movement of the female and the control logic is further configured to not store the representations of measurements of the first temperature at the data store when one of the following conditions is true:
 (a) variation in previous movement measurements exceeds a predetermined value;
 (b) at least one movement measurement exceeds a predetermined value.

14. A system as claimed in claim 1, further comprising a second physiological data set including movement data for the female and the data processor is operable to disregard at least some of the measurements of the first temperature which were measured when one of the following conditions was true:
 (a) variation in measurements represented by the movement data exceeded a predetermined value;
 (b) measurements represented by the movement data exceeded a predetermined value.

15. A system as claimed in claim 1, wherein the first temperature sensor is a skin temperature sensor, the data logger device further comprises a second temperature sensor and the control logic is further configured to store representations of measurements of the second temperature by the second temperature sensor at the data store.

16. A system as claimed in claim 15, wherein the second temperature sensor is arranged to measure an ambient temperature of the female and the data reader device is configured to process each measurement of the first temperature sensor in dependence on a corresponding measurement by the second temperature sensor so as to form an estimate of a core body temperature of the female.

17. A system as claimed in claim 1, wherein the data processor is further configured to form the estimate of the basal body temperature in dependence on at least one of the following:
 (a) a rate of change in measurements of the first temperature;
 (b) a rate of change in the rate of change in measurements of the first temperature.

18. A system as claimed in claim 1, wherein the data logger is arranged to transmit at least some of the first physiological data set to the data reader by wired or wireless transmission.

19. A system as claimed in claim 1, wherein the data processor is operable to receive a second physiological data set for providing an indication of the point of ovulation and the data processor is further arranged to combine the estimated basal body temperature of the female and the second physiological data set so as to form said indication of the point of ovulation.

20. A system as claimed in claim 1, wherein the data processor is configured to estimate the basal body temperature using the rate of change of the first temperature with time.

21. A system for determining a basal body temperature of an animal or human, the system comprising:
 a data logger device comprising:
  a first temperature sensor for measuring a first body temperature;
  a data store;
  control logic configured to store representations of first body temperature measurements at the data store as a first physiological data set; and
  a transmitter operable to transmit at least some of the first physiological data set;
 a data reader device comprising a receiver operable to receive at least some of the first physiological data set from the data logger device; and
 a data processor arranged to access the first physiological data set and to extrapolate a decrease in first body temperature indicated during a sleep period so as to estimate a basal body temperature of the user representative of a minimum body temperature.

22. A system as claimed in claim 21, wherein said sleep period is a period of low movement of at least a predetermined length.

23. A system as claimed in claim 22, wherein the predetermined length is 30 minutes.

24. A system as claimed in claim 21, wherein data representing variations in temperature of the animal or human taken outside the said sleep period is not used in estimating the basal body temperature.

25. A system as claimed in claim 21, wherein the data processor is further arranged to estimate the basal body temperature by comparing first body temperature measurements taken during a sleep period with temperature-time curves taken during previous sleep periods.

26. A system as claimed in claim 21, wherein the data processor is configured to estimate the basal body temperature using the rate of change of the first body temperature with time.

27. A method for determining a point of ovulation in a female, the method comprising:
- storing at a data store as a first physiological data set representations of first body temperature measurements of the female measured by a first temperature sensor;
- accessing by a data reader device at least some of the first physiological data set stored in said data store;
- estimating, using a data processor associated with said data reader device, a basal body temperature of the female from the accessed first physiological data set by extrapolating a decrease in first body temperature indicated during a sleep period so as to estimate a basal body temperature of the user representative of a minimum body temperature; and
- forming an indication of the point of ovulation from said estimated basal body temperature.

\* \* \* \* \*